United States Patent
Clark et al.

[11] Patent Number: 5,910,137
[45] Date of Patent: *Jun. 8, 1999

[54] LAYERED ABSORBENT PRODUCTS

[75] Inventors: Tracey A. Clark, North Brunswick; Mary Gail Ciesielski, East Brunswick; Kathleen D. O'Donnell, Somerville, all of N.J.

[73] Assignee: McNeil-PPC, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/723,741

[22] Filed: Sep. 30, 1996

Related U.S. Application Data

[63] Continuation of application No. 08/236,762, Apr. 29, 1994, abandoned.

[51] Int. Cl.$^6$ ..................................................... A61F 13/15
[52] U.S. Cl. .................... 604/387; 604/385.1; 604/386; 604/389
[58] Field of Search ...................... 604/365, 378, 604/385.1–387, 389–394

[56] References Cited

U.S. PATENT DOCUMENTS

| | | |
|---|---|---|
| 2,929,379 | 3/1960 | Poulsen . |
| 3,367,334 | 2/1968 | Testa . |
| 3,570,492 | 3/1971 | Bettencourt . |
| 4,019,517 | 4/1977 | Glassman . |
| 4,022,210 | 5/1977 | Glassman . |
| 4,072,150 | 2/1978 | Glassman . |
| 4,405,310 | 9/1983 | Karami ................................. 604/383 |
| 4,425,130 | 1/1984 | DesMarais ............................. 604/389 |
| 4,505,707 | 3/1985 | Feeney .................................. 604/393 |
| 4,576,597 | 3/1986 | Hlaban .................................. 604/390 |
| 4,592,943 | 6/1986 | Cancian et al. ..................... 428/171 |
| 4,622,089 | 11/1986 | Lauritzen ............................. 156/250 |
| 4,623,341 | 11/1986 | Roeder ................................. 604/385 |
| 4,713,134 | 12/1987 | Mays et al. .......................... 156/181 |
| 4,774,124 | 9/1988 | Shimalla et al. ..................... 428/171 |
| 4,787,947 | 11/1988 | Mays ................................... 156/160 |
| 5,256,466 | 10/1993 | Berringan et al. .................... 428/166 |
| 5,429,630 | 7/1995 | Beal et al. ............................ 604/389 |
| 5,429,631 | 7/1995 | Grenier ............................. 604/385.1 |

FOREIGN PATENT DOCUMENTS

| | | |
|---|---|---|
| 67 465 | 12/1982 | European Pat. Off. . |
| 557 047 | 8/1993 | European Pat. Off. . |
| 43 22 550 | 4/1994 | Germany . |
| 60-175230 | 11/1985 | Japan . |
| 5-177 | 1/1993 | Japan . |
| 5049660 | 3/1993 | Japan ................................... 604/387 |
| 2144995 | 1/1987 | United Kingdom . |
| 90/04376 | 5/1990 | WIPO . |
| 93/18728 | 9/1993 | WIPO . |

OTHER PUBLICATIONS

European Search Report for PCT/US95/04485, dated Aug. 21, 1995.

*Primary Examiner*—Robert A. Clarke
*Assistant Examiner*—K. M. Reichle

[57] ABSTRACT

A multilayered absorbent feminine hygiene product which is configured for releasable attachment to a user's garment has a plurality of absorbent pads. Each of the absorbent pads has an absorbent layer to contain absorbed fluid and a barrier layer to prevent absorbed fluid from leaking completely through the individual pad. The first, lowermost pad in the product is configured for releasable attachment to a user's garment. Additional pads in the product are releasably attached above the first pad to form a stacked or layered product. The pads may be adhesively, thermally, compressively, or mechnically bonded. Preferably, the multilayered product includes three absorbent pads.

19 Claims, 6 Drawing Sheets

LAYERED ABSORBENT PRODUCTS

This is a continuation of application Ser. No. 08/236,762, filed Apr. 29, 1994, now abandoned.

FIELD OF THE INVENTION

The present invention relates to a multilayered absorbent feminine hygiene product. In particular, it relates to a stacked or layered product containing individual absorbent pads which are releasably attached one to another.

BACKGROUND OF THE INVENTION

Absorbent products have long been used as feminine hygiene products. Discretion in the use of these products has been a goal of manufacturers and users alike. Absorbent pads and napkins used for feminine hygiene provide some specific capacity for absorbing body fluids. Once soiled, a product must be replaced by an unsoiled product. Unfortunately, a woman is not always at home or otherwise conveniently near a supply of these absorbent products, and it may be necessary for her to keep a minimal supply of products with her. Thus, feminine hygiene products have been manufactured to be carried conveniently in a woman's purse or pocketbook. These products have also been manufactured in convenient, individual packages to keep the product clean until use. However, more discrete ways to keep a ready supply of feminine hygiene products handy are constantly sought.

Poulsen, U.S. Pat. No. 2,929,379, suggested that a woman might carry a supply of three sanitary napkins in a sanitary napkin product having multiple layers. Aside from the multiple layers of absorbent pads which made up the sanitary napkin product, it incorporated cloth tabs which extended from the front and rear of the absorbent pad which were secured to a belt. This belt was separately worn about the user's waist. The use of the belt in conjunction with sanitary napkins allowed the napkins to be held closely to the user's body. The plurality of absorbent layers of the Poulsen product are stacked and attached in one general location proximate the front of the sanitary napkin product. The back of the upper individual layers was not anchored to the adjacent layer. It was constrained only by the nature of the belted product.

In more recent times, belted feminine hygiene products have generally been replaced by products which are releasably secured to a user's undergarments by means of a layer or strip of pressure sensitive adhesive disposed upon a garment-facing surface of the product. In addition, new and thinner products, including thin sanitary napkins and panty liners, have been developed. Panty liners may be used for applications other than those for which traditional sanitary napkins were designed. These feminine hygiene products are substantially thinner than conventional sanitary napkins and have a substantially concentrated absorbent volume. Thin feminine hygiene products therefore, have less of the absorbent fluff layer which helps to provide flexibility to the product.

Most feminine hygiene products have a body-facing absorbent side and a garment facing barrier side. A pressure sensitive adhesive is generally disposed on the garment facing side as one or more lines to provide attachment means to removably fix the product to the garment. This pressure sensitive adhesive is protected from contamination until use with a piece of release liner. When the product is to be used, the user must first remove the release liner and dispose of it. The disposal of a piece of release liner with each panty liner increases the waste generated by the use of these products. Thus, it is desirable to reduce the amount of release liner used in conjunction with panty liners in an era of increased environmental awareness.

Absorbent products have a finite absorbent capacity, and they must be periodically replaced. Manufacturers continue to search for products which are easily carried by a user, are convenient and discrete. One solution is discussed in Takao et al., Japanese Utility Model 5-177 (Y2), which discloses a panty liner product having three single layers stacked and secured together. The bottom panty liner has a conventional adhesive disposed for positioning the product in the crotch area of a user's undergarment. Each remaining layer is releasably attached to the layer below it in the stack by adhesive or embossing (heat sealing) means. The Takao et al. reference illustrates that the adhesive is to be applied in two relatively small areas proximate the front and rear ends of the layer, or adjacent layers may be embossed at four discrete positions of the layers.

Additionally, Fuji Kikaku, Ltd, Japanese Utility Model Application No 60-175230 (U), discloses a multilayered sanitary napkin product having smaller pads stacked on top of larger pads and secured with two discrete strips of adhesive tape. Again, these strips are at the ends of the pad layers.

After a substantial amount of research into the problems associated in developing panty liners having several removable absorbent layers, it has been discovered that panty liners having only one local attachment point between individual layers are susceptible to substantial movement of the unsecured portions of the panty liner layers. The forces acting on such pads tend to displace at least the topmost pad as the user moves. The displacement allows the pad to intrude into the area between the buttocks where it can be wedged, causing discomfort and painful chafing. This movement presents a major problem for users of thinner panty liners. Merely adding a second minor spot of adhesive cannot guarantee a firm attachment of the topmost panty liner through intermediate panty liner layers to the user's undergarment.

Using two small areas of adhesive spaced apart at the ends of a panty liner pad presents an additional problem. The adhesive may effectively attach adjacent pads at the adhesive application sites, but the adhesive cannot always prevent separation of the pads away from the application sites. Thus, when the application sites are located at the panty liner pad ends, the center section of adjacent pads can separate, causing problems similar to those identified above. Finally, while it is important that the absorbent layers of the panty liner product be secured together, the final product should be flexible enough to generally conform to the user to reduce chafing and other irritation.

Therefore, a new and useful panty liner product is needed having a plurality of absorbent pads which are releasably attached together in a secure manner. It is desirable that the product be flexible and comfortable to wear.

SUMMARY OF THE INVENTION

The present invention relates to an absorbent feminine hygiene product configured for releasable attachment to an undergarment. The product has several individual absorbent pad layers releasably joined together. Each of the absorbent pads has an absorbent layer and a liquid-impermeable barrier layer. An upper surface of each absorbent pad is defined by the top surface of the absorbent layer. A bottom, garment-facing surface of a first absorbent pad is configured for releasable attachment to a user's garment. A bottom surface of a second absorbent pad is releasably attached to the top absorbent surface of the first absorbent pad in a manner to prevent separation of significant portions of the absorbent pads during use. Preferably, the absorbent pads are releasably attached using attachment means which have a plurality of attachment points or areas distributed about the contact area of adjacent pads. Thus, in a preferred embodiment, the attachment means covers a substantial portion of the contact area. The first absorbent pad can be releasably attached to a user's garment with a first separation force, and the second absorbent pad is releasably attached to the first absorbent pad with a second separation force, less than the first separation force.

In a preferred embodiment, each absorbent pad has a peripheral edge, and at least a portion of the peripheral edge of the second absorbent pad extends beyond at least a corresponding portion of the peripheral edge of the first absorbent pad.

In another preferred embodiment, the absorbent pads are stacked together and releasably attached with a layering adhesive. The layering adhesive is applied at low coating weights per unit area in a pattern over a substantial portion of the contact area between adjacent pads. The application pattern of the layering adhesive keeps the individual pad layers of the product secured one to another and prevents gapping, curling and other separation during use.

While individual pad layers are secured to adjacent layers, the individual pad layers can, nonetheless, slip along one another when subjected to shear forces. This allows the absorbent product of the present invention to remain as flexible as some single pad absorbent products of the same class which are commercially available.

Unless otherwise stated, when used in conjunction with adhesive coating and/or terms relating to surface areas, the term "coverage" and related forms of the word including the verb "to cover" as used in the specification and claims includes both a continuous layer of adhesive and a regular or random pattern of an adhesive coating having void areas. In particular, "coverage" includes the application of a pattern of discrete dots, fibrils, continuous or discontinuous lines, etc., over an area or substantially enclosing an area, even if the adhesive particles, fibers, etc., coat only a fraction of that area. Thus, the area "covered" by an adhesive is that area defined by the boundaries of the applied adhesive pattern.

As used in the specification and the claims, the phrase "contact area" means the area of a first absorbent pad contacted by a second absorbent pad stacked on the first.

DETAILED DESCRIPTION OF THE PREFERRED EMBODIMENT

The absorbent product of the present invention has a plurality of releasably attached absorbent pads which are stacked together. The pads may be attached by any means which provide sufficient attachment strength to maintain product integrity during use. Preferably, the stacked pads are held together in a manner to prevent separation of significant portions of the absorbent pads during use. Thus, the attachment means should be able to continue to hold adjacent pads together under both shear and peel forces likely to be encountered during product use.

The attachment means may be adhesive, thermal or compressive such as heat sealing and embossing, and mechanical such as fiber entanglement or hook-and-loop type fasteners. Preferably, the attachment means provides varied attachment strength between adjacent pads and between the bottom pad and the user's garment to which it is attached. The first, garment-facing pad may be releasably attached to the user's garment with a first attachment strength, and a second absorbent pad is releasably attached to the first pad with a second attachment strength which is preferably less than the first attachment strength. Additional pads may be releasably attached in a stacked manner to the top of the second absorbent pad with attachment strengths, preferably not greater than the second attachment strength.

Figure 5:
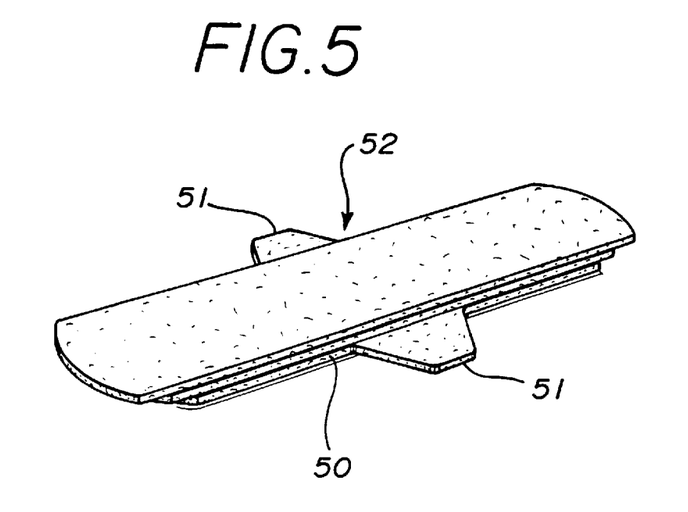
FIG. 5 shows a perspective view of an alternative embodiment of the present invention incorporating laterally extending tabs proximate a center section of a bottom absorbent pad.
Figure 6A:
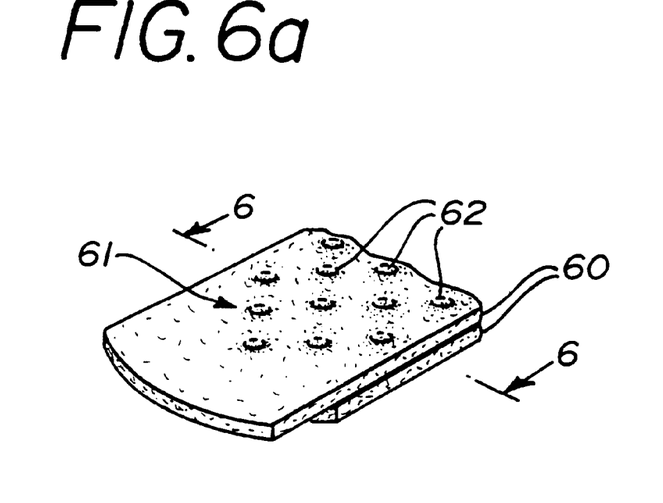
FIG. 6a shows an alternative embodiment of the present invention in which the absorbent pad layers are releasably attached with a thermal bonding pattern.
Figure 6B:
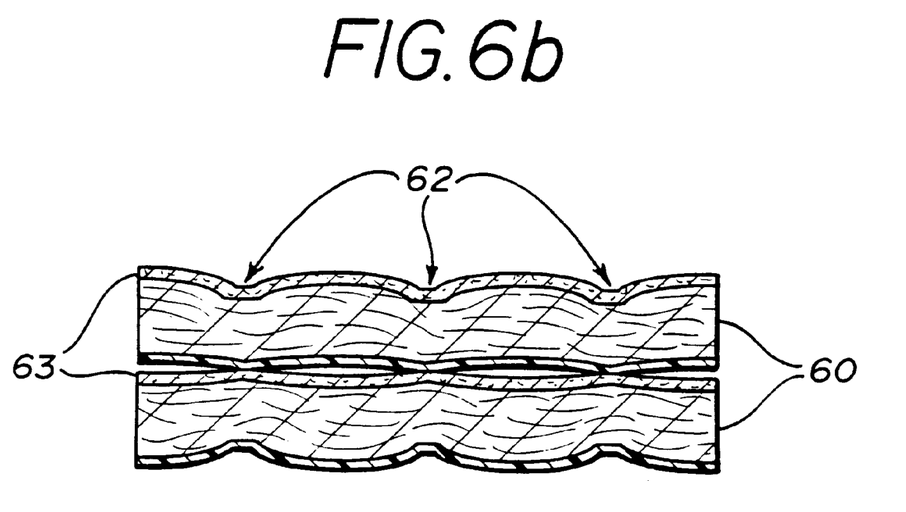
FIG. 6b illustrates a cross-section of FIG. 6a along line 6—6.

The absorbent pads which are stacked in the absorbent product may be of any geometry normally used in the feminine hygiene field, including strip-like (See FIG. 1), dog-bone or hourglass shaped, and the like. Referring to FIG. 5, the pads 50 may also have laterally extending tabs 51 proximate a center portion 52 of the pad 50 for at least partially wrapping around a user's undergarment. In the stacked multilayered absorbent product, each pad may have at least substantially similar geometry, i.e., all strip-like or hourglass shaped. As used herein, the term "at least substantially similar geometry" includes identical geometry. Where the pads are of substantially similar geometry, they may have slightly different proportions. Thus, successive absorbent pads may be proportionately longer or shorter in length. Alternatively, the pads may have different geometry. For example, only the first, garment-facing absorbent pad may have tabs 51. In another embodiment, the ratio of length to width may be substantially altered, e.g., one layer long and narrow, and a second layer short and wide.

Figure 4A:
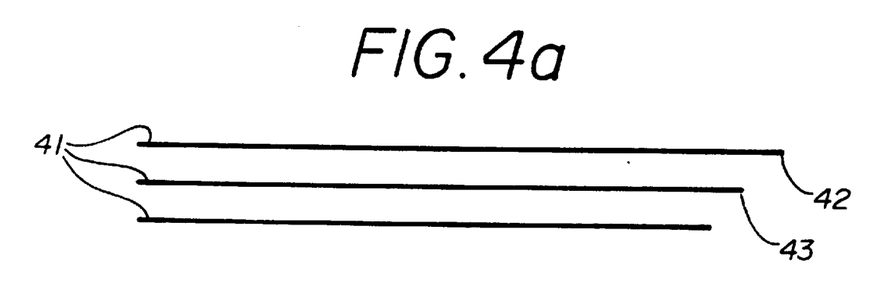
FIGS. 4a and 4b show line depictions of two alternative embodiments of the arrangement of absorbent pads having overlapping portions.
Figure 4B:
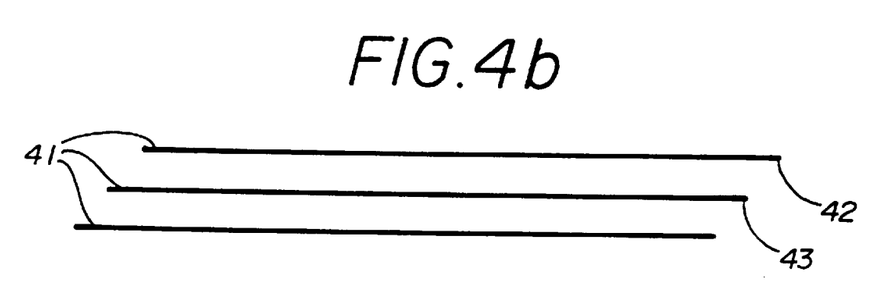

Referring to FIGS. 4a and 4b, the geometry of the individual absorbent pads 41 may therefore allow for partial or complete overlap of one absorbent pad in relation to an adjacent pad. Preferably, at least a portion of the peripheral edge 42 of an upper absorbent pad overlaps at least a portion of an adjacent lower absorbent pad 43 in the stacked product. This overlap can protect the lower pad from soiling or staining by body fluids during use and facilitates the removal of a soiled pad from the pad immediately below it. Where the absorbent product is constructed from identically-sized individual pads, the overlap of at least one edge of the uppermost pad is achieved by staggering the pads as in FIG. 4b. Where the pads are of different sizes, the pads may be stacked in a manner to cover each pad with the absorbent pad immediately above it. Thus, the first, garment-facing pad may be completely covered by a second absorbent pad, and a third absorbent pad may completely cover the second absorbent pad. Additionally, each upper pad may extend beyond the peripheral edge of the pad immediately below it in the stack.

The individual absorbent pads of the multilayered product are preferably relatively thin. This allows several absorbent pads to form an absorbent product which will not be too thick for the average product user. The individual pads may be panty liners, thin sanitary napkins or even ultrathin sanitary napkins, and possibly thin incontinence pads. Preferably, the individual absorbent pads of the invention have a thickness of less than about 10 mm, more preferably, less than about 5 mm, and most preferably, less than about 2.5 mm.

The absorbent product of the present invention remains flexible. Indeed, preferred multilayered absorbent products have-a flexural resistance according to the test method of Example V, below, in the range of equivalent absorbent products. Thus, multilayered sanitary napkins have a flexural resistance in the range of conventional sanitary napkins, and multilayered panty liners have a flexural resistance in the range of conventional panty liners. Preferred multilayered panty liners have a flexural-resistance of less than about 0.25 lbs, and more preferred multilayered panty liners have a flexural resistance of less than about 0.2 lbs.

Figure 1:
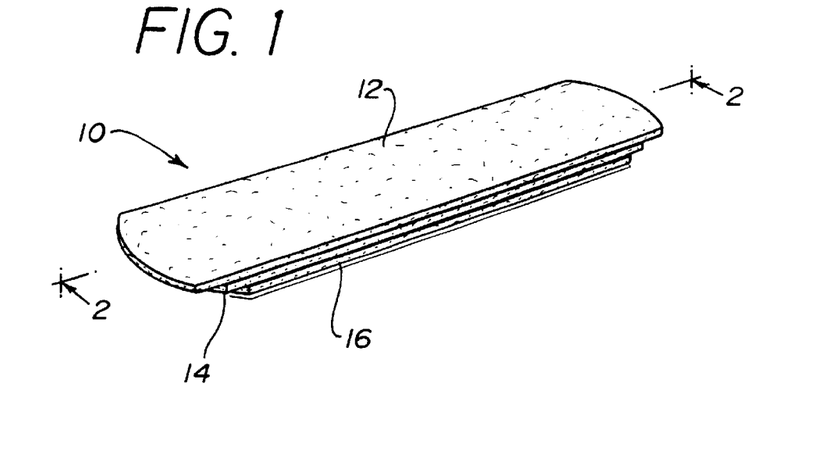
FIG. 1 shows a perspective view of a multilayered panty liner according to the present invention.
Figure 2:
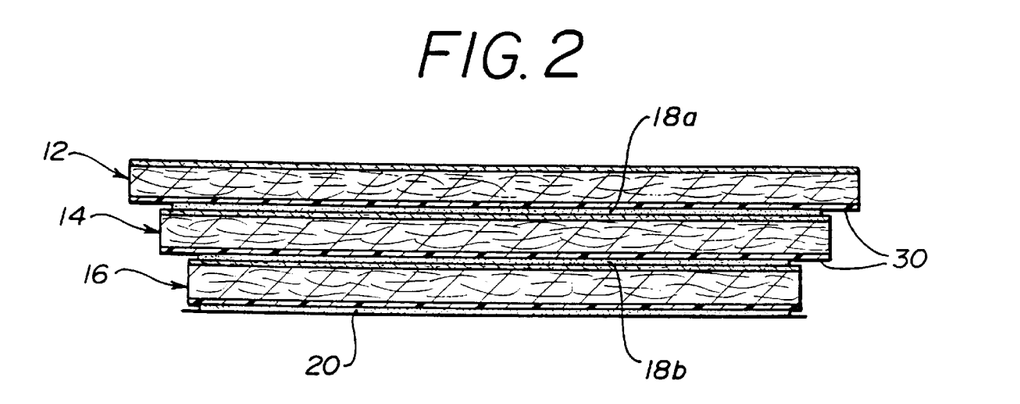
FIG. 2 shows a cross section of the multilayered panty liner along line 2—2 in FIG. 1.

Referring to FIG. 1, there is depicted, a multilayered panty liner 10 having a top pad 12, a center pad 14 and a bottom pad 16. FIG. 2 shows a cross section of the multilayered panty liner 10, including the attachment means (for example adhesive 18a, 18b, which releasably attach the top pad 12 to the center pad 14 and the center pad 14 to the bottom pad 16, respectively. In addition, the bottom pad has a positioning means 20, illustrated in FIG. 2 as an adhesive layer.

Individual Absorbent Pads

Figure 3:
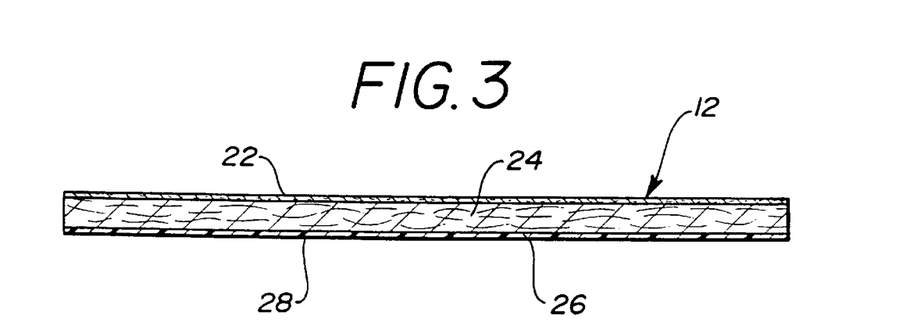
FIG. 3 shows a cross section of an individual pad along the line 2—2 in FIG. 1.

A detail of an individual absorbent pad is depicted in FIG. 3. The individual absorbent pad 12 comprises a top, liquid permeable layer 22, an absorbent structure 24 and a bottom, barrier film 26. The absorbent pad 12 can be any conventional panty liner pad. To keep lower pads clean until use, the absorbent pads 12,14,16 preferably decrease in size from top to bottom. In a particularly preferred embodiment, the top pad 12 is about 6 to 8 inches (15 to 20 cm) long and 1¾ to 2½ inches (4.4 to 6.4 cm) wide, the center pad 14 is about 5¾ to 7¾ inches (14.6 to 19.7 cm) long and 1¾ to 2¼ inches (4.4 to 5.7 cm) wide and the bottom pad 16 is about 5 to 7½ inches (12.7 to 19 cm) long and 1½ to 2¼ inches (3.8 to 5.7 cm) wide. Examples of single layered panty liner products currently on the market include panty liners sold under the trademarks CAREFREE, KOTEX LIGHTDAYS, NEW FREEDOM, and ALWAYS and the like. These products generally have an absorbent structure 24, and a plastic barrier film 26. The absorbent structure may include several layers, or it may be a single layer having an upper liquid pervious surface. Preferably, the absorbent structure has several layers, the top layer forming the liquid pervious layer 22. The liquid permeable layer 22 may be a nonwoven fabric such as a spunbonded fabric, a thermal bonded fabric, a resin bonded fabric, the like; an apertured film such as those known by the trademarks DRI-WEAVE, RETICULONE, Apex, and the like; a densified top layer formed with hydrogen bonding; or any other suitable covering surface. The rest of the absorbent structure 24 may be cellulosic fibers, including wood pulp and cotton pulp; synthetic fibers, including polyolefins and polyesters; and the like. Preferably, the absorbent structure includes wood fluff pulp and about 5 to 80% of fusible, thermoplastic fibers. Useful absorbent structures and top surfaces are disclosed in Cancian et al., U.S. Pat. No. 4,592,943; Mays, et al. U.S. Pat. No. 4,713,134; Mays U.S. Pat. No. 4,787,947 and Shimalla et al., U.S. Pat. No. 4,774,124. The disclosures of which are herein incorporated by reference.

A particular preferred class of individual absorbent pads 12 is a fusible fiber pulp structure (FFP). It is constructed with a liquid permeable layer 22. In one embodiment, the layer 22 comprises a nonwoven fibrous web formed of staple hydrophobic textile fibers. Such fibers may be unified by being coated with a water-insoluble rubbery fiber-binding resin so that all of the individual fibers are substantially covered with a resin coat, thus bonding them together at their crossing points while leaving the interstices of the web unfilled.

The liquid permeable layer 22 can also be a porous, substantially planar flexible polymeric coating on the surface of a bonded staple hydrophobic fiber web or on the outermost surface of a lofty web of blended fibers in a pad construction wherein each component is essentially completely secured to adjacent components. Such a surface, due to the flatness of the polymeric coating, has an unusually soft, smooth feeling and is pleasing to the touch.

Preferably, the fibers of the liquid permeable layer 22 are thermoplastic or, more preferable, a mixture of two or more types of thermoplastic fibers having different melting points. Upon application of heat and pressure sufficient to melt at least one of the fiber types, the remaining unmelted fibers will be thermobonded or fused together into a porous web. This processing step is described more fully in Lauritzen, U.S. Pat. No. 4,622,089, hereby incorporated by reference.

The fibrous materials found to be satisfactory in the making of the liquid permeable layer have been found to be blends of two thermoplastic fibers having distinguishable melting temperatures. Bicomponent fibers, fibers with an inner core of a thermoplastic fiber, e.g., polyester, surrounded by an outer sheath of thermoplastic e.g., polyethylene, having a melting point much lower than the core, have been found to be the best fibers to work with from processing and performance standpoints in this class of absorbent pads. It is also conceivable that the material for liquid permeable layer 22 may be coformed blends of pulp fluff and thermoplastic fibers, e.g., polypropylene.

It has been found to be acceptable to use fibrous materials for the liquid permeable layer 22 having a denier in the range of from about 1.0 to about 4.0. Fiber length for the liquid permeable layer 22 has been found to be satisfactory if in the range of from about 0.5 inches to about 2.5 inches.

The resulting web is a thin, pliable, resilient, porous, cloth-like fabric whose top surface has a soft, smooth, pleasing, tactile quality. This web may be fed directly and continuously into the manufacturing process for the individual absorbent pad of this invention. It may also be collected and stored for later use.

In heat bonded relationship with liquid permeable layer 22 is an absorbent structure 24 comprising a blend of thermoplastic fibers in this class of absorbent pads. It is preferable that the thermoplastic fibers of absorbent structure 24 be a mixture of two or more types of thermoplastic fibers having different melting points. Bicomponent fibers having a melting point much lower than the core, have been found to be the best fibers to work with from processing and performance standpoints. Like layer 22 above it, upon application of heat and pressure sufficient to melt at least one of the fiber types, the remaining unmelted fibers will be thermobonded or fused together into a porous web.

It is also preferable to include cellulosic pulp fibers with the thermoplastic fibers in absorbent structure 24. Since thermoplastic fibers, without further treatment, are essentially hydrophobic, absorbent structure 24 will not effectively draw fluid away from liquid permeable layer 22 absent some hydrophilic material. It is important to have sufficient pulp to absorb fluid. An acceptable amount of pulp for effective absorbency is from about 20% to about 95% by weight. Conversely, an acceptable amount of thermoplastic fibers is from about 5% to about 80% by weight. A preferred amount of pulp would be in the range of from about 20% to about 60% by weight (with thermoplastic fibers being in the range of from about 40% to about 80%).

A second fusible fiber layer, made from the same or similar material as liquid permeable layer 22, may be used to "sandwich" the absorbent structure 24. Pulp fluff is very dusty. By sandwiching the absorbent layer containing pulp between two fibrous thermoplastic layers, the dust in the operating environment is greatly reduced. In this construction, the layer first laid down in manufacture is generally smoother.

The ratio of thermoplastic fiber to pulp fluff may be characterized by comparing the total amount of pulp and thermoplastic fibers in both the total absorbent structure including the liquid permeable layer 22 and the bottom outside "sandwiching" layer (not shown) and absorbent structure 24. Since they are to be in heat bonded relationship, it is preferable that, when looking at the fusible fiber layers 22 together with absorbent structure 24, there is at least 35% by weight thermoplastic fibers. It is more preferable that there be at least 60% by weight thermoplastic fibers in both "sandwiching" layers.

The fibrous materials found to be satisfactory in the making of the absorbent structure 24 are the same or similar fibrous materials used for the liquid pervious layer 22. Bicomponent polyester/polyethylene fibers have been found to be the best fibers to work with from processing and performance standpoints in this class of absorbent layers. Although it has been found that using fibers having a denier of about 1.8 in liquid pervious cover layer 22 results in improved comfort, it is not necessary to use fibers of this denier for absorbent structure 24. Although any denier in the range of from about 1.0 to about 4.0 will suffice, from a cost standpoint a denier of from about 2.5 to about 3.5 will yield good performance with acceptable manufacturing costs. Fiber length for absorbent structure 24 has been found to be satisfactory if in the range of from about 0.5 to about 2.5 inches.

It is clear that the major distinctions between the liquid permeable layer 22 and absorbent structure 24 is the presence of pulp in absorbent structure 24 and the possibility of finer denier fibers in liquid permeable layer 22. However, since the ranges for each layer overlap, it is possible and acceptable to use the same denier fibers for both the liquid permeable layer 22 and absorbent structure 24. In such a case, there is no real need for two separate and distinct layers. Instead, it is possible to construct the pad using one layer that has a body contacting surface and a surface which faces barrier film 26 (which is described in more detail below). In such a case, however, it is important to remember that the body contacting surface should be substantially devoid of pulp.

The plastic barrier film may be any barrier film useful in the panty liner and sanitary napkin art. Useful films include, without limitation, polyolefin films such as polyethylene and polypropylene; polyvinyl films such as polyvinyl acetate, polyvinyl chloride, and polyvinylidene chloride; copolymeric films such as ethylene-vinyl acetate, and blends or laminates of one or more of the above polymers. Preferred barrier films include ethylene-vinyl acetate/polyethylene laminate films and polypropylene films.

Attachment Means

The absorbent pads 12, 14, 16 generally and particularly described above are stacked and releasably attached to form the absorbent product 10 of the present invention. The pads 12, 14, 16 may be attached by any attachment means which provide sufficient attachment strength to maintain product integrity during use. The attachment means may be adhesive 18a, 18b (as illustrated in FIG. 2), thermal or compressive such as heat sealing and embossing, mechanical such as fiber entanglement or hook-and-loop type, and the like.

The attachment means may be a single attachment zone such as a solid area, a series of lines, a pattern of attachment points which cover an area, and the like. Preferably, if a plurality of attachment zones are used, each attachment zone is within 2 inches of an adjacent attachment zone. This helps to limit the separation of adjacent absorbent pads in the product according to the present invention.

In a preferred embodiment, the attachment zones may also include void areas. These void areas preferably have a major axis of less than about ½ inch and more preferably less than about ¼ inch.

Adhesive

In one preferred embodiment, the adhesive may be applied to the bottom surface 28 of an individual absorbent pad 12, 14, 16. Preferably, the adhesive is disposed upon a substantial portion of the contact area of the bottom surface 28. The adhesive is also preferably applied at relatively low coating levels, i.e., low coating weights per unit area. The low coating weight over relatively large surface area provides a secure attachment between the adjacent absorbent pads in the multilayered product.

The relative adhesion between the adjacent absorbent pads in the panty liner product in comparison with the strength of the attachment means 20 between the panty liner product and the garment to which it is attached is a characteristic of one embodiment of the present invention. Preferably, the attachment strength between adjacent absorbent pads 12, 14, 16 should be less than the strength of the attachment means 20 between the panty liner product and the garment. In the case of adhesive attachment to the garment (positioning adhesive), this can be achieved by selective use of adhesives for both the layering adhesive and the positioning adhesive 20. For example, an adhesive which adheres more strongly to cotton than synthetic polymers would adhere more strongly to cotton undergarments. In a particularly preferred embodiment, the attachment strength between layers decreases with increasing vertical distance from the bottom pad. Thus, in a three layered panty liner product, the positioning adhesive 20 or other attachment means between the product and garment would have the highest attachment strength, the attachment strength of the layering adhesive 18b between the bottom absorbent pad 16 and the center absorbent pad 14 would be less than the attachment strength between the bottom pad 16 and the undergarment, and the attachment strength of the layering adhesive 18a between the top pad 12 and the center pad 14 would be less than that between the center pad 14 and the bottom pad 16. In addition, the attachment strength between adjacent pads in the construction is preferably substantially less than the force necessary to delaminate the individual absorbent pads.

In general, the layering adhesive has an average peel strength of at least about 0.02 lb/in according to the test method of Example II, below, to allow it to maintain the structural integrity of the panty liner product during use. More preferably, the layering adhesive has an average peel strength of at least about 0.04 lbs/in and a peak peel strength of less than about 5 lbs/in according to the test method of Example I to allow the layering adhesive to maintain the integrity of the panty liner product without resulting in delamination of the individual absorbent pads when the user removes the top pad in a stack. Most preferably, the layering adhesive has an average peel strength of greater than about 0.04 lbs/in and a peak peel strength of less than about 3 lbs/in.

Generally, these adhesive peel strength ranges relate to an average attachment strength of at least about 0.04 lb for an absorbent pad layer of the present invention. This can be determined for the product according to the test method of Example II. The peak attachment strength of the absorbent pad layer is preferably less than about 10 lbs for the product, more preferably, less than about 5 lbs when measured according to the test method of Example I.

Preferably, the layering adhesive covers at least about 40% of the contact area of the bottom surface 28. More preferably, it covers about 60% to 95% of the contact area, and most preferably, about 75% to 95%. It is preferred that the layering adhesive not be applied at the extreme longitudinal ends of the barrier film. The lack of adhesive at the longitudinal ends of the barrier film provides finger tabs 30 to enable a user to more easily separate adjacent absorbent pads.

The layering adhesive can be classified by method of setting: solvent-releasing, e.g., emulsion or organic solvent based; curing, e.g., radiation cure, electron beam, or catalytic cure; or hot melt. Preferred adhesives are pressure sensitive adhesives (PSA). PSAs can allow adjacent pads to be reattached if they are prematurely separated. However, PSAs have the potential of transferring to the cover material on an absorbent layer and forming a somewhat tacky surface on the cover material. Therefore, if a PSA is used as the layering adhesive, it is preferred that it be selected such that a minimal amount, if any, of the PSA transfers to the cover material from the barrier film. If a non-PSA is used, it is preferred that the adhesive remain flexible after setting so that the cover material remains supple and relatively soft to the touch. A representative, non-limiting list of useful PSAs includes those based on natural rubber, styrene/butadiene latex, A-B-A block copolymer, butyl rubber and polyisobutylene, acrylics including vinyl acetate-acrylate copolymers, vinyl ether polymers, polyalkene polymers, polyurethane, ethylene-vinyl acetate copolymers and polypropylene including atactic polypropylene. A representative, non-limiting list of useful non-PSAs includes latexes based on the above-listed resins and hot melts based on these resins. Preferably, the adhesive is a PSA, and more preferably, the PSA is an A-B-A block copolymer, an acrylic resin, or an ethylene-vinyl acetate copolymer. Most preferably, the PSA is based on an A-B-A block copolymer. The adhesive can be applied to the absorbent pad in any manner known to the ordinary practitioner. Such application methods include, without limitation, spraying, roll coating, slot coating, gravure rolling, etc.

The selection of the adhesive for use as a layering adhesive 18a, 18b is also dependent upon the composition of the bottom surface 28 and the covering layer 22 of the individual absorbent pads 12, 14, 16 which make up the multilayered product. In particular, if a PSA is used, adhesive transfer can be noticeable. Also, if the cover sheet and barrier film of adjacent absorbent pads are formed from similar material, there may be a greater tendency for a PSA to transfer to the cover sheet.

Generally, the adhesives described above adhere to bottom surfaces 28 formed by barrier films 26. Preferably, the adhesives adhere strongly to the selected barrier film 26. The adhesives described above also adhere to the cover sheet 22, although it is preferred that the adhesion to the cover sheet 22 be less than that to the barrier film 26.

The choice of adhesive used to practice the invention depends in part on the barrier film, and perhaps more particularly, the cover sheet used. The selection of adhesive to use with a given cover sheet and barrier film will be readily determined by one of ordinary skill in the art. Preferably, the adhesive adheres strongly to the barrier film, less strongly to the cover sheet of an adjacent absorbent pad, and does not transfer from the barrier film to the cover sheet. As a guideline, it has been determined that A-B-A block copolymers work well with polyolefin barrier films and nonwoven cover sheets. These block copolymers also work with apertured film cover materials. Acrylics, EVA and other similar adhesives also work with these materials.

According to a preferred embodiment of the present invention, a block copolymer PSA, such as that available from National Starch and Chemical Company as product #34-5539, or an atactic polypropylene adhesive, such as LUNATACK D 3457C by H. B. Fuller Co., is used at low coating weight over a large surface area. Preferably, the adhesive is applied at about 0.5 mg/in$^2$ to 6 mg/in$^2$. More preferably, the adhesive is applied at about 0.5 to about 4 mg/in$^2$. Most preferably, the adhesive is applied at about 0.75 mg/in$^2$ to substantially cover the bottom surface of the top absorbent pad and at about 1 mg/in$^2$ to substantially cover the bottom surface of the middle absorbent pad in a three-layered product. The bottom pad may be anchored to a user's garment with about 8 mg/in$^2$ of a block copolymer adhesive such as that sold under the product number HM-1972 positioning adhesive from H. B. Fuller Co. The coating weight is determined by weighing the absorbent pad before and after application of the adhesive and dividing the weight (in grams) by the area covered by the adhesive.

Thermal and/or Compressive Means

In another embodiment, thermal and/or compressive attachment means can be used to releasably attach the absorbent pads in the multilayered product. Thermal attachment means include, without limitation, heat sealing, embossing at elevated temperatures, ultrasonic sealing, and the like. Compressive attachment means include, without limitation, cold flow embossing, crimping, and the like. Generally, the thermal attachment means include an element of compressive force, as well. Thus, embossing with applied heat is included in this category of attachment means.

Figure 7A:
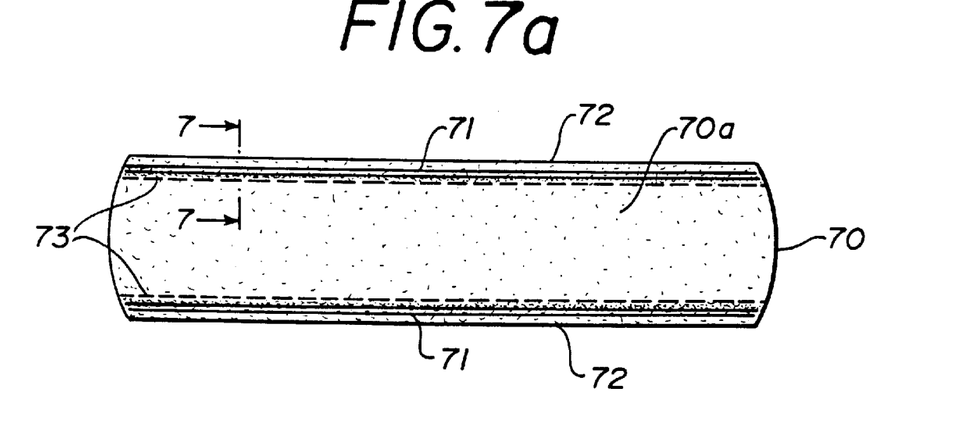
FIG. 7a shows a top view of an alternative embodiment of the present invention in which the absorbent pad layers are releasably attached by embossing/heat sealing along the side edges and in which the absorbent pads are removed by tearing along perforations inside the heat sealed lines.
Figure 7B:
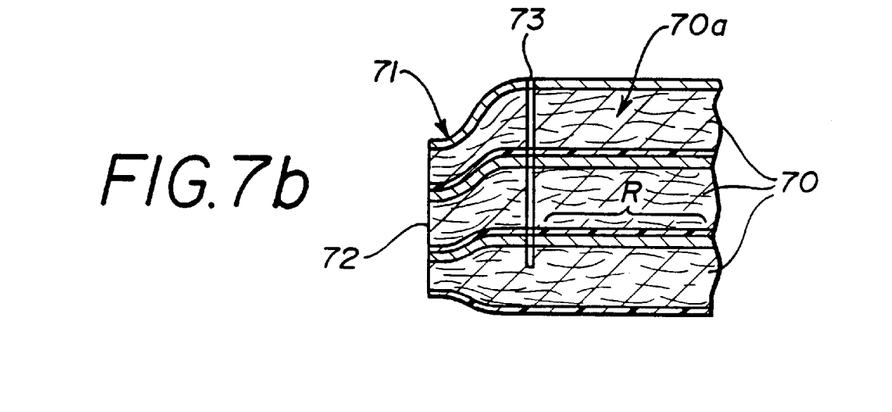
FIG. 7b shows a cross-section of FIG. 7a along line 7—7.
Figure 7C:
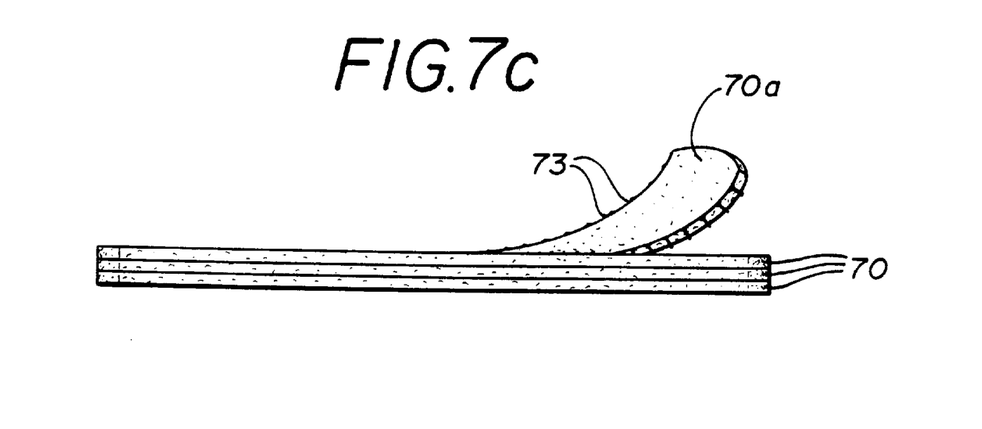
FIG. 7c shows a side view of the embodiment of FIG. 7a during the removal of the top absorbent pad.

Referring to FIGS. 6a–7c, the absorbent pads 60, 70 may be heat sealed or embossed with applied heat in a pattern (See FIGS. 6a and 6b) as described for the adhesive attachment means, or the absorbent pads 60, 70 may be heat sealed/embossed along their side edges (See FIGS. 7a–7c). If the thermal attachment means are applied in a pattern 61 over a substantial surface of the absorbent pads 60, the individual heat sealed or embossed attachment points 62 should leave a soft surface on the upper, absorbent surface 63 to avoid irritating the user. The thermal attachment means 71 can also be used to substantially permanently seal the side edges 72 of the pads 70 in the absorbent product while allowing a perforated portion 70a of the pad defined by perforations 73 to be removed as illustrated in FIG. 7c. In addition, a combination of thermal and adhesive attachment can be used. An example of such a combination would be to apply an adhesive in the region designated as R in FIG. 7b to more securely attach the center portions of the absorbent pads during use.

Mechanical Attachment Means

Figure 8:
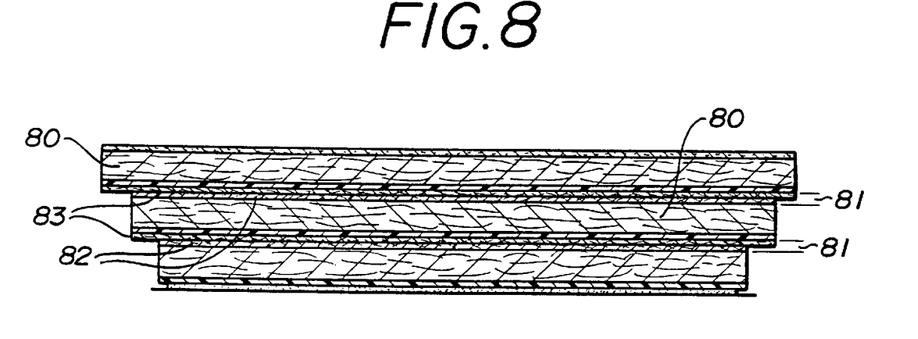
FIG. 8 shows a cross section along line 2—2 of FIG. 1 of an alternative embodiment employing fiber entanglement.
Figure 9:
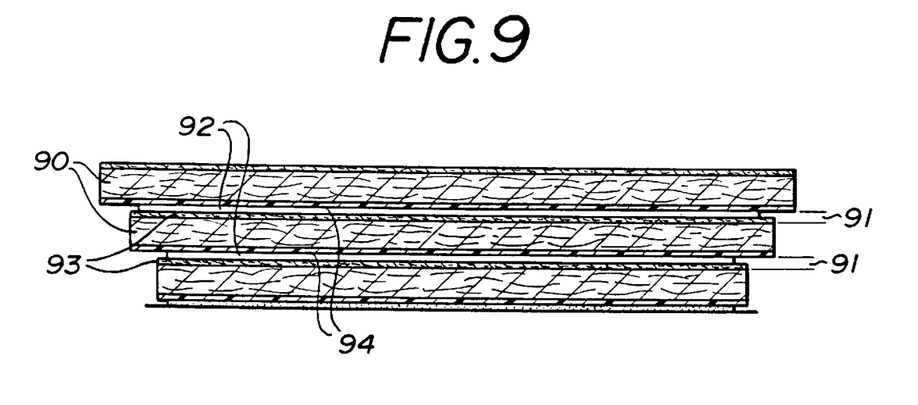
FIG. 9 shows a cross section along line 2—2 of FIG. 1 of an alternative embodiment employing hook-and-loop type fasteners.

In another embodiment illustrated in FIGS. 8 and 9, mechanical attachment means 81, 91 may be used to releasably attach the absorbent pads 80, 90 in the multilayered product. Mechanical attachment means include, without limitation, fiber entanglement, hook-and-loop type fasteners and the like. Fiber entanglement involves the use of a fibrous top surface 82 in conjunction with a fibrous bottom surface 83 of adjacent absorbent pads 80 in the stacked product. In this embodiment, fibers from these adjacent surfaces come into close contact and become entangled to releasably attach the two layers 82, 83 together. Any fibrous surfaces can be used in this embodiment provided that the fibers forming the surface have sufficient crimp to enable the fibers from adjacent layers to become entangled and catch. Examples of fibers useful in this invention include natural fibers having crimp such as cotton, wool, and the like; and synthetic fibers which have a coiled or crimped nature such as rayon, polyester, nylon, and the like. Preferred synthetic fibers are relatively thick and resilient, having a denier of about 1 to 15, preferably about 3 to 10. This allows the entanglement of the adjacent layers to have sufficient attachment strength to hold the product together during use. In a preferred embodiment of this invention, the adjacent fibrous layers 82, 83 of adjacent absorbent pads 80 are different, e.g., 3 in top surface 82 and 10 in bottom surface 83 to allow the fibers of one layer to intrude to a greater extent into the fibers of the adjacent layer. However, it may also be desirable to use fibrous layers having similar fibers to allow the entanglement to be more uniform.

Alternative mechanical attachment means includes hook-and-loop type fasteners 91. These fastener systems are well known to those of ordinary skill in the art, are widely available and include fasteners sold under the trademark VELCRO and the like. These fasteners generally have a first attachment surface 92 having an array of relatively rigid hooks (not shown in detail) and a second attachment surface 93 of looped fibers. In using this type of attachment means, the array of hooks can be secured on the bottom or barrier side 94 of the individual absorbent pads 90, and the second attachment surface 93 can be located on the top, absorbent surface of the individual absorbent pads 90. The second attachment surface 93 can comprise looped fibers, or the fibers can result from a relatively loose, woven or nonwoven fabric. It is merely required that the array of hooks can contact and hold securely onto the second fibrous attachment surface.

Alternative Embodiments

Figure 10:
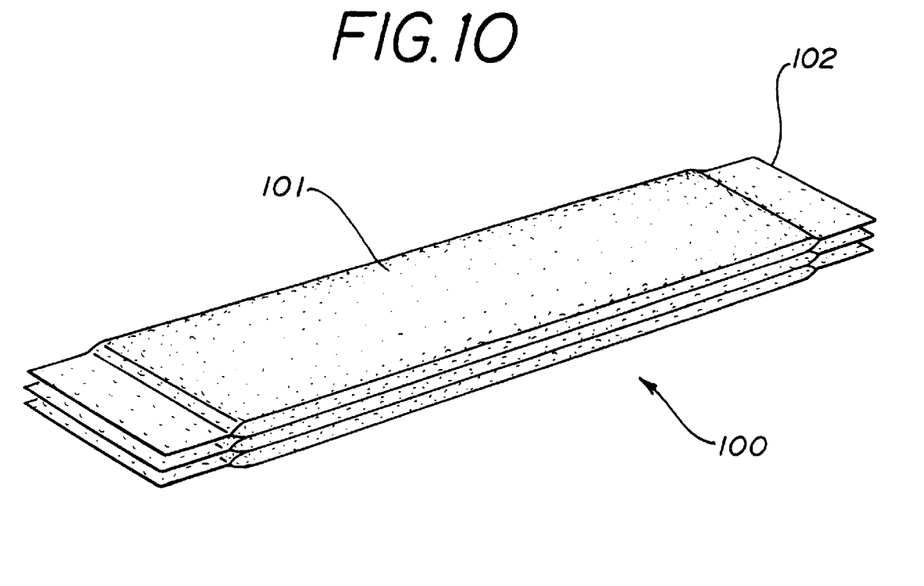
FIG. 10 shows a perspective view of a multilayered thin sanitary napkin according to the present invention.

While the above discussion refers primarily to panty liner products, the practitioner will recognize with reference to FIG. 10 that the multilayered product of the present invention can be a thin sanitary napkin 100. Commercially available thin napkins include SURE & NATURAL THIN, ULTRA THIN, and PRIMA napkins, STAYFREE THIN and ULTRA THIN napkins, ALWAYS ULTRA napkins, and KOTEX ULTRA THIN napkins, etc. These products generally have a liquid permeable overwrap 101 which encloses an absorbent structure and a liquid impervious barrier sheet (not shown). The overwrap 101 is sealed together about the periphery or at the ends 102 of the product. The materials of the exterior surfaces of thin sanitary napkins may be similar to those used in panty liners. The dimensions of the sanitary napkin are generally larger than corresponding panty liner. For example, the napkin pads may be about 6 to 13 inches (15 to 33 cm) long and about 2 to 5 (5 to 13 cm) inches wide. The teaching of this invention relating to panty liners can therefore be used to create a multilayered sanitary napkin as well.

Method of Use

In use, a consumer would remove the release liner which protects the positioning adhesive from the multilayered panty liner product and secure the product in the crotch area of her undergarment. After some period of time when the top absorbent pad has become soiled, the user can simply remove the soiled pad to expose the next absorbent pad. This procedure can be continued until all absorbent pads have been soiled and a new multilayered product is needed.

The present invention will be further understood by reference to the following specific Examples which are illustrative of the composition, form and method of producing the multilayered panty liner product of the present invention. It is to be understood that many variations of composition, form and method of producing the panty liner product would be apparent to those skilled in the art. The following Examples, wherein parts and percentages are by weight unless otherwise indicated, are only illustrative.

EXAMPLE I

A series of delamination tests were run on several commercial panty liners to determine a maximum commercially useful peel strength of the layering adhesive.

Samples were prepared as follows:

A 7"×2" strip of Permacel Professional Grade Gaffer's Tape was cut, one end was folded onto itself to create a ½"

tab. A 2½"×3½" piece of release paper was placed on the tape, with the 2½" side parallel to the 2" edge of the tape, leaving a 4" length of adhesive exposed. The adhesive coated side of the tape was then placed on the surface of a test product such that the sides of the tape strip lined up with the edges of the product, the folded tab of the tape did not overlap with the test product but extended past its end to provide a constant thickness over the surface of the product, and the edge of the exposed adhesive did not overlap any crimp or curve on either end of the test product.

The test product was then placed in a Jenkins press between two platens heated to 100° F. and pressed at 150 psi for 3 minutes. One minute after removal from the heated platens, the sample is secured to a TMI tester sled and the top cover is clamped for peel testing. The TMI tester is engaged to remove the top cover at a rate of 1200 in/min. The force of removal, as well as adhesive tear-out and/or transfer, is recorded. The TMI tester is a Release and Adhesive Tester, Model #80-14, available from Testing Machines, Inc. of Amityville, N.Y. In order to get more detailed output than the test method describes, the dial strain gauge on the TMI Release and Adhesive Tester was replaced with an Entran Devices, Inc. model ELF-TC500-10 10 lb. load cell. The load cell was fed into a Tektronix TEK 2430A digital oscilloscope and the force profile over the entire peel was captured and plotted.

Each prepared sample was placed on the sled with the barrier side of the product down. The end of the test product closest to the tab on the Gaffer's Tape was anchored to the sled using 3M Duct Tape. The release paper patch was removed from the Gaffer's Tape and the tabbed end of the tape was held by jaws attached to the load cell. As each sample was run, the force profile over the peel of the test sample, the maximum force over the peel and the mean force were captured by the oscilloscope and plotted.

Between each sample tested the oscilloscope was zeroed to within 0.04 V using the mean force read-out at zero load.

The oscilloscope was calibrated using the dial strain gauge to verify two or three force read-outs at the start of each test session. All tests were run at 1 volt, =1 pound.

The samples tested were ALWAYS LONG with DRI-WEAVE (longs were used to avoid tape over the crimped ends and still allow a 4" peel), ALWAYS SHEER CONFIDENCE (cut to a 2" width to avoid edge effects), KOTEX LIGHTDAYS WRAPAROUND (cut to a 2" width), and Product A, an example of the present invention.

Product A was produced by forming a 2.5 oz/yd$^2$ absorbent structure having a first veneer layer of 0.3 oz/yd$^2$ BASF 1040 bicomponent fiber, 1.8 denier, nonwoven fabric, a 1.9 oz/yd$^2$ air-laid core of 1.14 oz/yd$^2$ BASF 1039 bicomponent fiber, 3.0 denier, and 0.76 oz/yd$^2$ ITT XJ-HM E-Type Cellulosic Fluff Pulp (a 60:40 ratio by weight of bicomponent fiber:fluff pulp), and a second veneer of 0.3 oz/yd$^2$ BASF 1039 bicomponent fiber, 3.0 denier, nonwoven fabric. The absorbent structure is thermobonded by passing hot air (about 300° F.) through the structure from the BASF 1039 veneer side to the BASF 1040 side for about 2 sec. The absorbent structure has a "smooth side" comprising the BASF 1040 veneer which is formed against a screen in the preparation of the structure. The surface opposite the "smooth side" of the absorbent structure is adhered to a 1.25 mil PE/EVA, laminate barrier film using about 3 mg/in$^2$ National Starch #34-5539 adhesive coated on the EVA (top) side of the laminated barrier film. The resultant absorbent pad is thermally bonded about its perimeter to seal the absorbent structure to the barrier film, maintaining its integrity.

Each type of sample had a characteristic force profile. For example, the KOTEX LIGHTDAYS products have a very sharp force increase at the very beginning of the peel to a peak force value and then a sharp drop to a relatively steady peel. However, the Product A samples have a jump in force at the beginning when the veneer initially tears, which holds for a short time creating a broader peak than the KOTEX products and another more narrow peak at the end when the seal breaks. Depending on the Product A sample's seal strength, the veneer tear force peak may or may not correspond to the maximum force displayed. The results shown in Table 1 were calculated using the peak force of the veneer tearing as the inherent strength of the material and assume a normal distribution.

TABLE 1

INHERENT STRENGTH OF PRODUCT SURFACE MATERIALS*

|  | Mean Max. Force of Tear (lb/2" Width) | Std. Dev. | 99% Conf. Int. (lb/2" Width) | Normalized Mean Max. Force of Tear (lb/in) | Normalized 99% Conf. Int. (lb/in) |
|---|---|---|---|---|---|
| ALWAYS with DRIWEAVE Pantiliner | 3.61 | 0.44 | 2.70–4.52 | 1.81 | 1.35–2.26 |
| ALWAYS SHEER CONFIDENCE Pantiliner | 7.11 | 0.70 | 5.67–8.55 | 3.56 | 2.84–4.28 |
| KOTEX LIGHTDAYS Pantiliner | 3.35 | 0.42 | 2.49–4.21 | 1.68 | 1.25–2.11 |
| Product "A" | 3.54 | 0.56 | 2.39–4.69 | 1.77 | 1.20–2.35 |

*Test run with 5 samples of each product

Under these test conditions the lower limit of each product type's confidence interval would be the upper limit for a layer adhesive's peel force. However, it would be wise to make the upper limit for the layer adhesive some safety factor below the lower confidence limit to ensure that there is no tearing of the surface of the lower layer. For example, calculating a 25% or 50% reduction of the lower confidence limit of the inherent strength of a product's surface material to determine the new upper limit for a layer adhesive's peel force would yield the values shown in Table 2, below.

TABLE 2

|  | Lower Limit of Surface Material Strength | | 25% Reduction Layer Adhesive Force Upper Limit | |
|---|---|---|---|---|
|  | lb/2" Width | Normalized lb/in | lb/2" Width | Normalized lb/in |
| ALWAYS with DRIWEAVE Pantiliner | 2.70 | 1.35 | 2.03 | 1.01 |
| ALWAYS SHEER CONFIDENCE Pantiliner | 5.67 | 2.84 | 4.25 | 2.13 |
| KOTEX LIGHTDAYS Pantiliner | 2.49 | 1.25 | 1.87 | 0.93 |
| Product "A" | 2.39 | 1.20 | 1.79 | 0.90 |

EXAMPLE II

A series of tests were run to determine the amount of adhesive which transfers from a barrier film to an adjacent cover sheet after aging with a 2 kg weight for 1 hour. The products were formed as follows:

TOP LAYER: 6.5" long, rectangular with curved ends.
The absorbent pad used in the top layer was prepared in the same manner as Product A of Example I with the following changes: The absorbent structure had a basis weight of 3.3 oz/yd$^2$ and the air-laid core had a basis weight of 2.7 oz/yd$^2$.

BOTTOM LAYER: 6.0" long, rectangular with curved ends.
The absorbent pad used in the bottom layer was prepared from the same material as the top layer. In addition, 10 mg/in$^2$ of HM-1972 positioning adhesive from H. B. Fuller Co. was slot coated onto the bottom (PE) side of the barrier film in a pattern 5.25" long×1.75" wide.

Varying coating levels of a layering adhesive, National Starch #34-5539 adhesive, were spray coated on the bottom (PE) side of the barrier film of the top layer in a pattern covering the entire exposed surface.

TEST CONDITIONS

After preparation, samples were run on an INSTRON Model No. 1122 apparatus equipped with a moveable sled. The sample is placed in the test apparatus horizontally, and the leading edge of the sample is lifted to be attached to the test arm at a 90° orientation. Under the test conditions, the leading edge of the sample is pulled upwards at 12 in/min, and the moveable sled is moved at 12 in/min toward the point of separation of the sample to maintain the 90° orientation. A four inch peel was recorded. The results are shown in Table 3, below.

TABLE 3

| 90 DEGREE PEEL TEST RESULTS | | | | | | |
|---|---|---|---|---|---|---|
| COATING LEVEL (mg/in$^2$) | AVG. LOAD 4" PEEL (lb/2" W) | STD. DEV. | AVG. PEAK LOAD (lb/2" W) | STD. DEV. | NORMALIZED AVG. LOAD (lb/in) | NORMALIZED AVG. PEAK LOAD (lb/in) |
| 0.3 | — | — | — | — | — | — |
| 0.5 | .088 | .032 | .192 | .068 | 0.044 | 0.096 |
| .75 | .112 | .033 | .230 | .075 | 0.056 | 0.115 |
| 1.0 | .169 | .028 | .319 | .080 | 0.085 | 0.160 |
| 1.5 | .277 | .035 | .418 | .050 | 0.139 | 0.209 |
| 2.0 | .375 | .053 | .587 | .081 | 0.188 | 0.294 |
| 3.0 | .340 | .024 | .510 | .040 | 0.170 | 0.255 |
| 4.0 | .317 | .036 | .491 | .079 | 0.159 | 0.246 |
| 5.0 | .348 | .033 | .552 | .073 | 0.174 | 0.276 |
| 6.0 | .342 | .034 | .499 | .060 | 0.171 | 0.250 |
| 7.0 | .237 | .025 | .388 | .078 | 0.119 | 0.194 |
| 8.0 | .222 | .054 | .416 | .131 | 0.111 | 0.208 |

The amount of adhesive transfer increased with increasing coating level. All coating levels exhibited some trace of adhesive transfer. Transfer was extremely sparse at coating levels of 0.5 and 0.75 mg and was not present in most of the samples. Samples were prepared using 0.3 mg coating level but would not stay assembled long enough to be put in test. Samples were tested from coating levels of 0.5 mg to 8 mg. 5% of the 0.5 mg samples were positive for transfer and 10% were positive for the 0.75 mg samples. Between coating levels 2 and 6 mg, substantial fiber pull and bagging of the veneer occurred. Coating levels 7 to 8 mg had a significant decrease of fiber pull and bagging.

EXAMPLE III

In order to identify a maximum desired peel strength between individual absorbent pads, the adhesion between a bottom pad layer and a cotton undergarment was tested. The test pad layer was identical to the bottom layer of Example II.

90° peel strength testing was performed on 20 samples of this product using the procedures outlined in Example II. The results are shown in Table 4, below.

TABLE 4

| Avg. Load 4" Peel (lb/1.75 Width) | Std. Dev. | Normalized Avg. Load 4" Peel (lb/in) | Avg. Peak Load (lb/1.75 Width) | Std. Dev. | Normalized Avg. Peak Load 4" Peel (lb/in) |
|---|---|---|---|---|---|
| 0.24 | 0.03 | 0.14 | 0.34 | 0.05 | 0.19 |

The testing continued to evaluate the 90° peel strength between individual pad layers. The test products had 3 individual absorbent pads. The test data relates to the separation of a top pad from a middle pad while the middle and lower most pad remained adhered to a cotton undergarment panel.

Product B was prepared as follows

TOP LAYER: 6.5" long, rectangular with curved ends.

The absorbent pad used in the top layer was prepared in the same manner as Product A of Example I with the following changes: The barrier film was replaced with 0.6 mil polypropylene XP-544 FS/P, from Edison Plastics, Edison, N.J., the absorbent structure was adhered to the barrier film with 2.5 mg/in$^2$ of the National Starch #34-5539 adhesive, and 0.75 mg/in$^2$ of a layering adhesive, H. B. Fuller Co. HM-1972 hot melt adhesive was coated onto the bottom side of the barrier film in a pattern 5.25" long×1.75" wide.

MIDDLE LAYER: 6.25" long, rectangular with curved ends.

The absorbent layer used in the middle layer was prepared in the same manner as the top layer with the following changes: 0.75 mg/in$^2$ of the H. B. Fuller Co. HM-1972 hot melt adhesive was coated onto the bottom side of the barrier film in a pattern 5.5" long×1.75" wide.

BOTTOM LAYER: 6.0" long, rectangular with curved ends.

The absorbent pad used in the bottom layer was prepared in the same manner as the top layer with the following changes: 8 mg/in$^2$ of HM-1972 adhesive from H. B. Fuller Co. was coated onto the bottom side of the barrier film in a pattern 5.25" long×1.75" wide.

The products were assembled to be staggered at both ends.

Product C was prepared as follows

TOP LAYER: 6.0" long, rectangular with curved ends.

The absorbent pad used in the top layer was prepared in the same manner as the top layer of Product B with the following changes: The layering adhesive was 0.75 mg/in$^2$ H. B. Fuller Co. HM-1335X hot melt adhesive.

MIDDLE LAYER: 6.0" long, rectangular with curved ends.

The middle layer was the same as the top layer.

BOTTOM LAYER: 6.0" long, rectangular with curved ends.

The absorbent pad used in the bottom layer was prepared in the same manner as the top layer with the following changes: The positioning adhesive was 8 mg/in$^2$ of HM-1335X adhesive from H. B. Fuller Co.

90° peel strength testing was performed on 20 samples of each product using the procedures outlined in Example II. The data relate to removing the top pad layer from the middle pad layer and the middle layer from the bottom layer. The results are shown in Table 5, below.

TABLE 5

| | Avg. Load 4" Peel (lb./1.75" wid) | Std. Dev. | Normalized Avg. Load 4" Peel (lb/in.) | Avg. Peak Load 4" Peel (lb/1.75" wid) | Std. Dev. | Normalized Avg. Peak 4" Peel (lb/in) |
|---|---|---|---|---|---|---|
| Product "B" | | | | | | |
| Top Layer | 0.067 | 0.012 | 0.038 | 0.101 | 0.013 | 0.058 |
| Middle Layer | 0.059 | 0.013 | 0.034 | 0.087 | 0.013 | 0.050 |
| Product "C" | | | | | | |
| Top Layer | 0.036 | 0.009 | 0.021 | 0.032 | 0.008 | 0.018 |
| Middle Layer | 0.032 | 0.011 | 0.018 | 0.050 | 0.011 | 0.029 |

EXAMPLE IV

Individual absorbent pads were prepared in the same manner as Product A of Example I with the following changes: The surface opposite the "smooth side" of the absorbent structure is adhered to a 0.6 mil polypropylene barrier film using about 2.5 mg/in$^2$ National Starch #34-5539 adhesive coated on the top side of the barrier film. The pads were rectangular with curved ends, 6" long by 2" wide, and had a surface area of 11.5 in$^2$. Finished pads having no adhesive on the exposed barrier film surface were taped to a roll of paper and run through a spray coating line to be exposed to adhesive for the trial. The entire exposed surface of the barrier film was coated with adhesive (the taped area was considered to be negligible). The adhesive coating weights of the resulting samples of Products D–K are shown in Table 6.

TABLE 6

| Product | Adhesive | Coating Weight* | Peel Substrate |
|---|---|---|---|
| D | Atactic polypropylene[a] | 0.02 | FFP[f] |
| E | Atactic PP[a] | 0.04 | FFP[f] |
| F | Atactic PP[a] | 0.06 | FFP[f] |
| G | Ethylene-vinyl acetate[b] | 0.03 | FFP[g] |
| H | Acrylic[c] | N/A | FFP[g] |
| I | Acrylic[d] | 0.06 | FFP[f] |

TABLE 6-continued

| Product | Adhesive | Coating Weight* | Peel Substrate |
|---|---|---|---|
| J | SBS/SIS[e] | 0.02 | FFP[f] |
| K | SBS/SIS[e] | 0.04 | FFP[f] |

*grams/pad
[a]H. B. Fuller Co. LUNATACK D 3457C
[b]H. B. Fuller Co. LUNATACK D 3446C
[c]Schenectady International HRJ 10127
[d]Schenectady International HRJ 4326
[e]H. B. Fuller Co. 1280
[f]The structure of Product A, thermobonded @ 265° F., 2 sec.
[g]The absorbent structure of Product A.

The samples were prepared and tested (90° Peel) according to the test method described in Example II. The results are shown in Table 7.

TABLE 7

90 DEGREE PEEL TEST RESULTS

| PRODUCT | SAMPLE SIZE | AVG. LOAD 4" PEEL (lb/2" W) | STD. DEV. | PEAK LOAD (lb/2" W) | STD. DEV. | NORMALIZED AVG. LOAD (lb/in) | NORMALIZED AVG. PEAK LOAD (lb/in) |
|---|---|---|---|---|---|---|---|
| D | 5 | 0.024 | 0.001 | 0.044 | 0.002 | 0.012 | 0.022 |
| E | 20 | 0.060 | 0.013 | 0.098 | 0.019 | 0.030 | 0.049 |
| F | 5 | 0.111 | 0.011 | 0.160 | 0.021 | 0.055 | 0.080 |
| G | 20 | 0.101 | 0.019 | 0.165 | 0.028 | 0.051 | 0.083 |
| H[a] | | | | | | | |
| I[b] | 15[c] | 0.86 | 0.22 | 1.19 | 0.32 | 0.43 | 0.59 |
| J | 5 | 0.041 | 0.004 | 0.072 | 0.011 | 0.020 | 0.036 |
| K | 5 | 0.54 | 0.14 | 0.75 | 0.18 | 0.27 | 0.38 |

[a]Samples did not hold together for testing.
[b]All 20 samples exhibited adhesive legging and adhesive transfer.
[c]The cover tore on 5 of 20 samples; data based on 15 remaining samples.

The results suggest that several classes of adhesives are useful in the practice of the present invention. While the results using acrylic adhesives were not optimal, they suggest that acrylics can be formulated to work.

EXAMPLE V

The flexural resistance of three types of commercial panty liners and two embodiments of the present invention (Product L and Product M) was tested using the following test protocol:

Ten (10) samples of each product were obtained and conditioned for 24 hours at 72° F., 65% relative humidity. Each product sample was placed in a modified INSTRON Flexure Fixture, Model #2810-020. The fixture was modified to provide an adjustable roller gap, the gap was set at 1-½", and the Fixture was placed in the INSTRON Model #1122 test device described in Example II, above, with a 2,000 gram compression cell. A sample product was placed across the two rollers, and the transverse beam of the test device was adjusted to ½" above the rollers. The transverse beam descended toward the sample at 5"/min and continued until it had traveled 1-½" and the measured deflection values had passed the maximum value and began to decrease. The maximum force of the deflection was measured in grams and converted to lbs.

Product L was prepared in the same manner as Product B of Example III with the following changes: The seal pattern around the perimeter of the individual pad layers was a repeating flower pattern having a space of about 3 mm between adjacent flowers, the absorbent structure was thermobonded at 300° F. for 2 sec., and the layering adhesive is coated at 0.75 mg/in$^2$ in a pattern 2" by 5.75".

Product M was prepared in the same manner as Product L with the following changes: The seal pattern around the perimeter of the individual pad layers was a continuous embossed line, the absorbent structure is formed like that of Product A of Example I and the layering adhesive is coated at 0.75 mg/in$^2$ in a pattern 1.75" by 5.75".

The results of this testing are shown in Table 8, below.

TABLE 8

| Product | Average Flexural Force (lbs.) | Range (lbs.) |
|---|---|---|
| ALWAYS DRY-WEAVE | 0.029 | 0.028–0.030 |
| ALWAYS LIGHT DAYS Comfort Design | 0.065 | 0.060–0.073 |
| STAYFREE Panty Liner | 0.234 | 0.214–0.256 |
| Product L | 0.167 | 0.141–0.185 |
| Product M | 0.215 | 0.194–0.231 |

Both embodiments of the present invention fall within the flexural resistance range of currently available commercial panty liners.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent feminine hygiene product which is configured for releasable attachment to a user's garment, the product comprising three stacked individual absorbent pads, each of said pads comprising a top liquid-permeable surface opposite a bottom surface and having disposed therebetween an absorbent layer and a barrier layer, wherein a first of said absorbent pads having a peripheral edge, is configured for releasable attachment of the bottom surface of said first absorbent pad to the user's garment with a first attachment strength; a second of said absorbent pads having a peripheral edge and attachment means for releasably attaching the second pad to the top surface of the first absorbent pad, thereby forming a contact area between the first and second absorbent pads, with a second attachment strength, less than the first, in a manner to prevent separation of significant portions of the first absorbent pad from the second pad during use, at least a portion of the peripheral edge of the second absorbent pad extends beyond at least a corresponding portion of the peripheral edge of the first absorbent pad; and a third of said absorbent pads having a peripheral edge and attachment means for releasably attaching the third pad to the top surface of the second absorbent pad, thereby forming a contact area between the second and third absorbent pads, with a third attachment strength, not greater than the second, in a manner to prevent separation of significant portions of the second absorbent pad from the third absorbent pad during use, at least a portion of the peripheral edge of the third absorbent pad extends beyond at least a corresponding portion of the peripheral edge of the second absorbent pad, wherein the attachment means is a layering adhesive which is applied to form a plurality of attachment zones having void areas, each void area having a major dimension of less than about ½ inch; said attachment means covers at least about 40% of the contact area between the first and second absorbent pads and the second and third absorbent pads.

2. The absorbent product of claim 1 which has a flexural resistance of less than about 0.25 lbs.

3. The absorbent product of claim 1 wherein the adhesive is an atactic polypropylene adhesive or a block copolymer adhesive.

4. The absorbent product of claim 1 wherein the first absorbent pad has laterally extending tabs proximate a center portion of the pad for wrapping about the user's garment.

5. The absorbent product of claim 1 wherein the liquid-permeable surface of each pad is an apertured film.

6. The abosorbent product of claim 1 wherein the layering adhesive is disposed within the contact area in a manner to prevent rolling or curling of the first absorbent pad relative the second absorbent pad.

7. The absorbent product of claim 1 wherein the layering adhesive is selected from the group consisting of block copolymer adhesives, ethylene/vinyl acetate adhesives, polyolefinic adhesives, and acrylic adhesives.

8. The method of claim 1 wherein the layering adhesive is a pressure sensitive adhesive.

9. The absorbent product of claim 1 wherein each absorbent pad has a thickness of less than about 5 mm.

10. The absorbent product of claim 1 wherein the layering adhesive covers from about 60% to about 95% of the contact area.

11. A method of forming an absorbent feminine hygiene product which is configured for releasable attachment to a user's garment comprising the steps of:
   a) forming a plurality of individual absorbent pads, each of said pads having a peripheral edge and comprising a top liquid-permeable surface opposite a bottom surface and having disposed therebetween an absorbent layer and a barrier layer;
   b) configuring the bottom of a first of said absorbent pads for releasable attachment having a first attachment strength to the user's garment; and
   c) releasably attaching, at a second attachment strength, less than the first attachment strength, the bottom surface of a second of said absorbent pads to the top surface of the first of said absorbent pads, thereby forming a contact area between the first and second absorbent pads, wherein the attachment means is a layering adhesive which is applied to form a plurality of attachment zones having void areas, each void area having a major dimension of less than about ½ inch; said attachment means covers at least about 40% of the contact area between the first and second absorbent pads, wherein at least a portion of the peripheral edge of the second absorbent pad extends beyond at least a corresponding portion of the peripheral edge of the first absorbent pad.

12. The method of claim 11 wherein a peak attachment strength of the first absorbent pad to the user's garment is greater than about 10 lbs.

13. The method of claim 11 wherein an average attachment strength between the first and second absorbent pads is greater than about 0.04 lbs. and a peak attachment strength between the first and second absorbent pads is less than about 10 lbs.

14. The method of claim 11 which further comprises the step of releasably attaching at a third attachment strength, not greater than the second attachment strength, the bottom surface of a third absorbent pad to the top surface of the second of said absorbent pads.

15. The method of claim 14 wherein an average attachment strength between the second and third absorbent pads is at least about 0.04 lbs. and a peak attachment strength between the second and third absorbent pads is less than about 10 lbs.

16. The method of claim 11 wherein the absorbent product has a flexural resistance of less than about 0.25 lbs.

17. The method of claim 11 wherein each absorbent pad has a thickness of less than about 5 mm.

18. The method of claim 11 wherein the layering adhesive is applied at from about 0.5 mg/in$^2$ to about 6 mg/in$^2$.

19. The method of claim 11 wherein the layering adhesive covers from about 60% to about 95% of the contact area.

* * * * *

UNITED STATES PATENT AND TRADEMARK OFFICE
CERTIFICATE OF CORRECTION

PATENT NO. : 5,910,137
DATED : June 8, 1999
INVENTOR(S) : Tracey A. Clark et al.

It is certified that error appears in the above-indentified patent and that said Letters Patent is hereby corrected as shown below:

In claim 8, line 1, kindly delete "method" and insert --absorbent product--.

In claim 11, line 12, after "attaching" kindly insert --by attachment means--.

Signed and Sealed this

Twenty-third Day of November, 1999

Q. TODD DICKINSON

*Attest:*

*Attesting Officer*    Acting Commissioner of Patents and Trademarks